United States Patent [19]

Lamoreaux

[11] Patent Number: 4,459,266
[45] Date of Patent: Jul. 10, 1984

[54] AIR PURITY MONITORING SYSTEM

[76] Inventor: Charles L. Lamoreaux, 28012 Santona Dr., Rancho Palos Verdes, Calif. 90274

[21] Appl. No.: 337,259

[22] Filed: Jan. 5, 1982

[51] Int. Cl.³ .................. G01N 31/06; G01N 31/22
[52] U.S. Cl. ................................ 422/86; 128/719; 128/204.22; 422/88
[58] Field of Search ............ 128/719, 204.22; 73/23; 422/84, 85, 86, 88

[56] References Cited

U.S. PATENT DOCUMENTS

| | | | |
|---|---|---|---|
| 2,429,694 | 10/1947 | King | 422/86 |
| 2,489,654 | 11/1949 | Main-Smith et al. | 422/86 |
| 2,968,536 | 1/1961 | Smith | 422/86 |
| 3,009,785 | 11/1961 | Kaarlela | 422/86 |
| 3,539,302 | 11/1970 | Dreckmann | 422/86 |
| 3,924,442 | 12/1975 | Kerho | 73/23 |
| 4,040,783 | 8/1977 | Collin | 73/23 |
| 4,083,226 | 4/1978 | Ekstein et al. | 73/23 |
| 4,324,146 | 4/1982 | Born | 422/88 |

*Primary Examiner*—Michael S. Marcus
*Attorney, Agent, or Firm*—Henry M. Bissell

[57] ABSTRACT

A system for detecting specific contaminants in a gas such as compressed air and automatically indicating the degree of detected contamination. The system is selectively operable in either a PURGE mode or a TEST mode. During the PURGE mode, air flow rate is adjusted to a selected level by reference to a flow indicator. The system includes automatic timing control, operable in the TEST mode, to cause an air sample of prescribed volume to flow through a detection chamber. The system uses commercially available detector tubes which are specific to the particular contaminant suspected and which provide a positive indication of the degree of detected contamination for the volume of air in the sample. The system performs automatically in response to the operation of selected switches in a prescribed sequence, without any need for instrument calibration, thus permitting its use by virtually anyone inclined to use it. It is light and thereby portable, thus permitting it to be used in almost any location or under any conditions where compressed air for respiratory use is provided.

21 Claims, 4 Drawing Figures

AIR PURITY MONITORING SYSTEM

BACKGROUND OF THE INVENTION

1. Field of the Invention

The present invention is directed to monitoring the contaminant concentration in gases. More particularly, the present invention is directed to monitoring concentrations of selected contaminants in compressed air for respiratory use.

2. Description of the Prior Art

Many systems have been devised and are in use for determining contaminant concentrations in gases. Such systems often include pumps to meter a specified amount of gas through a testing material which changes color upon contact with a particular contaminant. These systems generally require a vial, which is inserted into the testing unit. A read-out is obtained from the vial which may be directly or indirectly used to determine the contaminant presence or concentration. Examples of such systems and the vials used as detector tubes are disclosed in a certain products bulletin of National Draeger, Inc., entitled "Gas and Vapor Detection Products".

Other systems in use in industry include in-line process sensors which determine a change in a characteristic of a gas being tested which is indicative of a change in contaminant concentration. These types of systems are useful where the contaminant itself is colored and, thus, changes in light reflection or transparency can be used to determine concentrations.

In other systems, electrical properties such as resistance or conductivity are measured against a standard to determine a concentration of the contaminant. Such prior art systems generally function quite well in the areas of suggested use. However, there is a need in the art for a system which is easily adaptable for use in measuring contaminant concentrations in compressed air and which can be used reliably by persons without particular skill or training in the use of air monitoring systems. It is apparent that with regard to compressed air which is used for breathing, for instance, the water vapor, oil, carbon monoxide, and carbon dioxide content of the compressed air should be monitored since the presence of such contaminants in even small amounts can be detrimental to the user. Thus, the present invention is directed to a system which can be easily utilized and will accurately test compressed air for the presence of various contaminants.

SUMMARY OF THE INVENTION

In brief, arrangements in accordance with the present invention constitute a system for detecting and measuring the concentrations of contaminants in compressed air. Such systems utilize particular contaminant indicators, known in the prior art, in the form of sealed glass tubes containing materials responsive to the presence of a particular contaminant. One suitable type of detector tube is available from National Draeger, Inc., 401 Parkway View Drive, Pittsburgh, Pa. Prior to use in arrangements of the present invention, the tips of the tubes are broken off to prepare the tubes for use.

Arrangements in accordance with the present invention comprise a housing containing the various air passages, valves and control circuitry and including a front face or panel on which are mounted a pair of air flow chambers having means for providing indications of flow rate and contamination, respectively, together with a plurality of control switches. A first one of the flow chambers includes a flow control valve having a knob accessible to the user and a standard flow meter for adjusting and indicating flow rate. The other flow chamber constitutes a test chamber having a closure member with a knob accessible to the user and designed to mount a standard detector tube in position to receive a preselected volume of air directed through the tube as an air sample and to provide an indication of contamination to the user. Automatic timing means, controllable for preselected distinct time intervals by one of the push button switches on the front of the panel, serves to control the air flow through the detector tube. Other front panel switches provide for purging the air system in accordance with operating instructions in preparation for contaminant monitoring.

The internal circuitry of the instrument includes a solenoid actuated valve for controlling air flow through the instrument and associated solenoid control circuitry equipped to apply an actuating voltage to the valve solenoid. The solenoid control circuitry includes a timer stage and respective "purge" and "stop" switches on the front panel. The timer may be activated to develop different preselected time intervals upon the closure of one or another of the test selector switches on the front panel.

BRIEF DESCRIPTION OF THE DRAWINGS

A better understanding of the present invention may be had from a consideration of the following detailed description, taken in conjunction with the accompanying drawings in which.

DESCRIPTION OF THE PREFERRED EMBODIMENT

Figure 1:
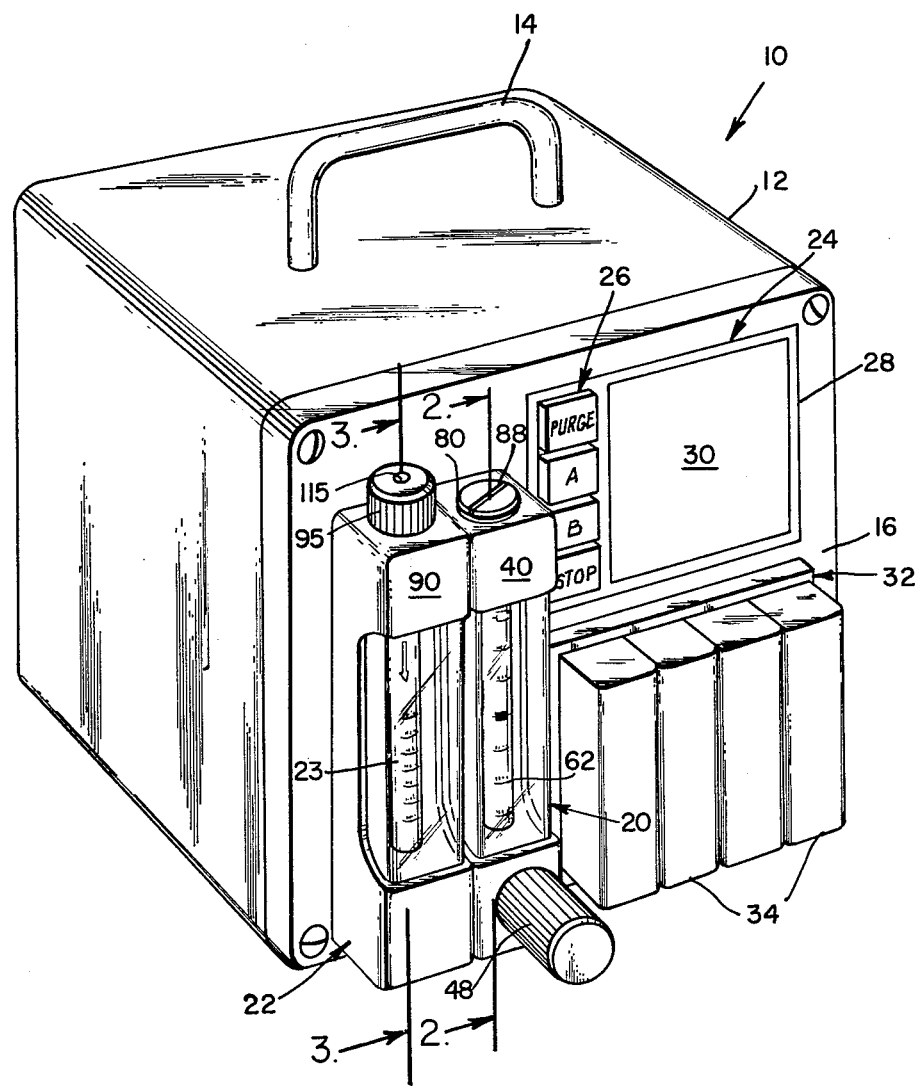
FIG. 1 is a perspective view of a monitoring system in accordance with the present invention.

As best shown in FIG. 1, the preferred embodiment of the air monitoring system 10 comprises a housing 12 having a handle 14, a front face 16 and couplings or connections (not shown) at the rear for attachment to pressure lines or hoses and to an electrical power source (typically 110 or 220 volts AC). By means of the air line coupling, the system 10 may be used with equal facility for determining the concentration of selected contaminants in compressed air from a compressor, from an accumulator or storage system, and from individual self-contained breathing apparatus (SCBA) bottles or other compressed air cylinders, merely by selection of appropriate adapters and fittings. The front face 16 mounts a flow meter assembly 20 and a detector tube test chamber assembly 22 with a detector tube 23 therein, together with a control module 24, shown as including a switch assembly 26 and associated sub-panel 28 bearing on its front face an instruction label 30. Below the control assembly 24 is positioned a storage module 32 having a plurality of storage containers 34 for up to 40 detector tubes ready for use in the contamination monitoring function. The system 10 is of extremely compact and convenient design, being a cube of 7 inches on a side and weighing eight pounds, thus being completely portable and ready to use at any time or place where 110 volt power is available or, in the alternative, by use of internal 12 volt battery power, which is optional.

Figure 2:
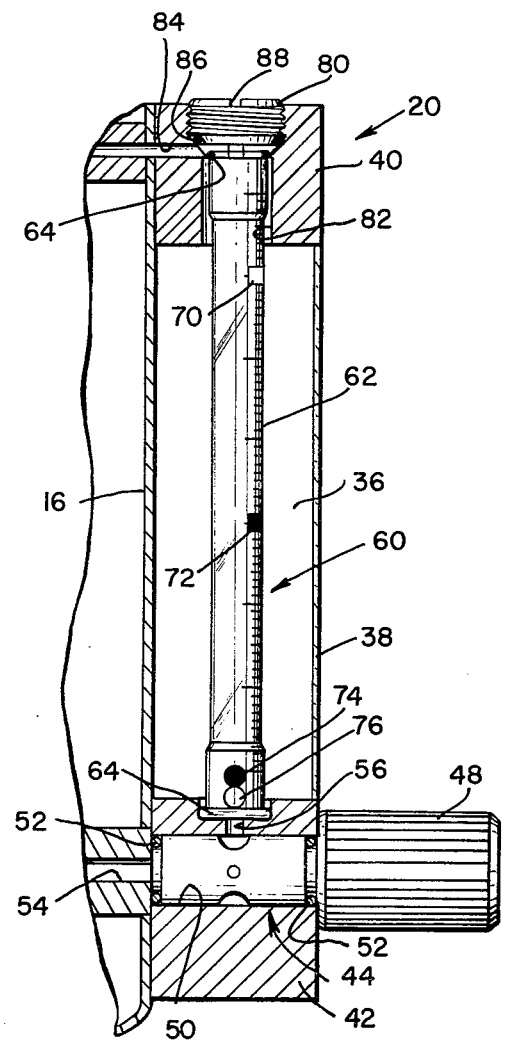
FIG. 2 is a sectional view of a portion of the monitoring system, taken along the line 2—2 of FIG. 1.

Referring to FIG. 2 for details of the flow meter assembly 20, the assembly is shown comprising a chamber 36 enclosed by a clear plastic cover 38 extending between upper and lower support blocks 40 and 42 mounted on the front face 16. The lower support block 42 includes a rotary, cartridge type, valve 44 having a central cylindrical member 46 to which is attached an external knob 48. The member 46 is mounted for rotation within a cylindrical chamber 50, sealed by O-rings 52 and having a central bore communicating with an inlet air passage 54 and, with the valve 44 in the open position, as shown in FIG. 2, with a passage 56 leading to a flow meter 60. The flow meter comprises a tube 62 extending between the upper and lower blocks 40, 42, and sealingly mounted thereto by O-ring seals 64 at the opposite ends of the tube 62. The flow meter tube 62 is of glass and is calibrated with dual scales: 0–200 cc/min. and 0–2000 cc/min. Near the upper end of the tube a silver marker 70 is placed on the glass at the calibration mark corresponding to 2.0 liters per minute. About mid way of the tube 62 a black marker 72 is located at a calibration mark indicating 0.2 liters per minute of air flow through the tube. The flow meter 60 further includes a pair of balls shown at the bottom of the tube 62, a black ball 74 and a silver ball 76. These are to simplify the setting of the air flow by means of the control valve 44 at a given selected air flow rate.

Shown in place within the upper support block 40 is a closure member 80, threadably mounted within the block 40 by mating threads 82. A port extends from the flow meter tube 62 through a central bore of the closure member 80 and communicates with an air passage 84 extending through the front panel 16. This air passage is sealed about the periphery of the closure member 80 by upper O-ring 86 and the adjacent O-ring 64. An Allen screw slot is shown at 88.

Figure 3:
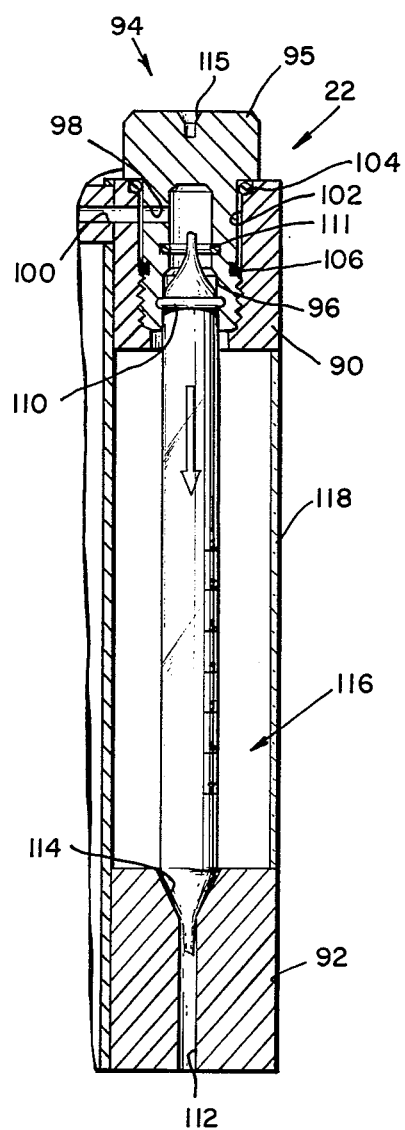
FIG. 3 is a sectional view of another portion of the monitoring system, taken along the line 3—3 of FIG. 1.

Referring to FIG. 3, the detector tube test chamber assembly 22 is shown comprising upper and lower support block 90, 92. Threadably mounted within the upper block 90 is a closure member 94 having a knob 95, a central bore 96 and internal air passage 98 communicating with external air passage 100 which is connected within the instrument to the passage 84 of FIG. 2. The closure knob 95 includes a central recess 115 provided to facilitate breaking the tips off a detector tube prior to use. There is a cylindrical space 102 between the outer surface of the closure member 94 and the inner face of the bore of support member 90, to insure communication for air flow between the passages 98 and 100 without regard to the rotational position of the closure member 94. This space 102 is sealed by upper and lower O-rings 104, 106.

Within the bore 96, O-rings 110 and 111 are positioned for the purpose of sealingly engaging a detector tube 23 when it is placed in position within the bore 96, thus sealing the upper end of the detector tube to the space within the upper part of the bore 96 and communicating with the air passage 98. The two O-rings are provided to accommodate different sizes of detector tubes.

The lower support block 92 contains an exhaust port 112 extending to atmosphere and having a cone or funnel-shaped portion 114 facing upward within the block 92. This funnel-shaped portion 114 is for the purpose of receiving the lower end of the detector tube when it is placed in the chamber 116 and retain it in sealing engagement within the bore 96 during a test. The chamber 116 is encased by a clear plastic cover 118 extending between the upper and lower support blocks 90, 92.

Figure 4:
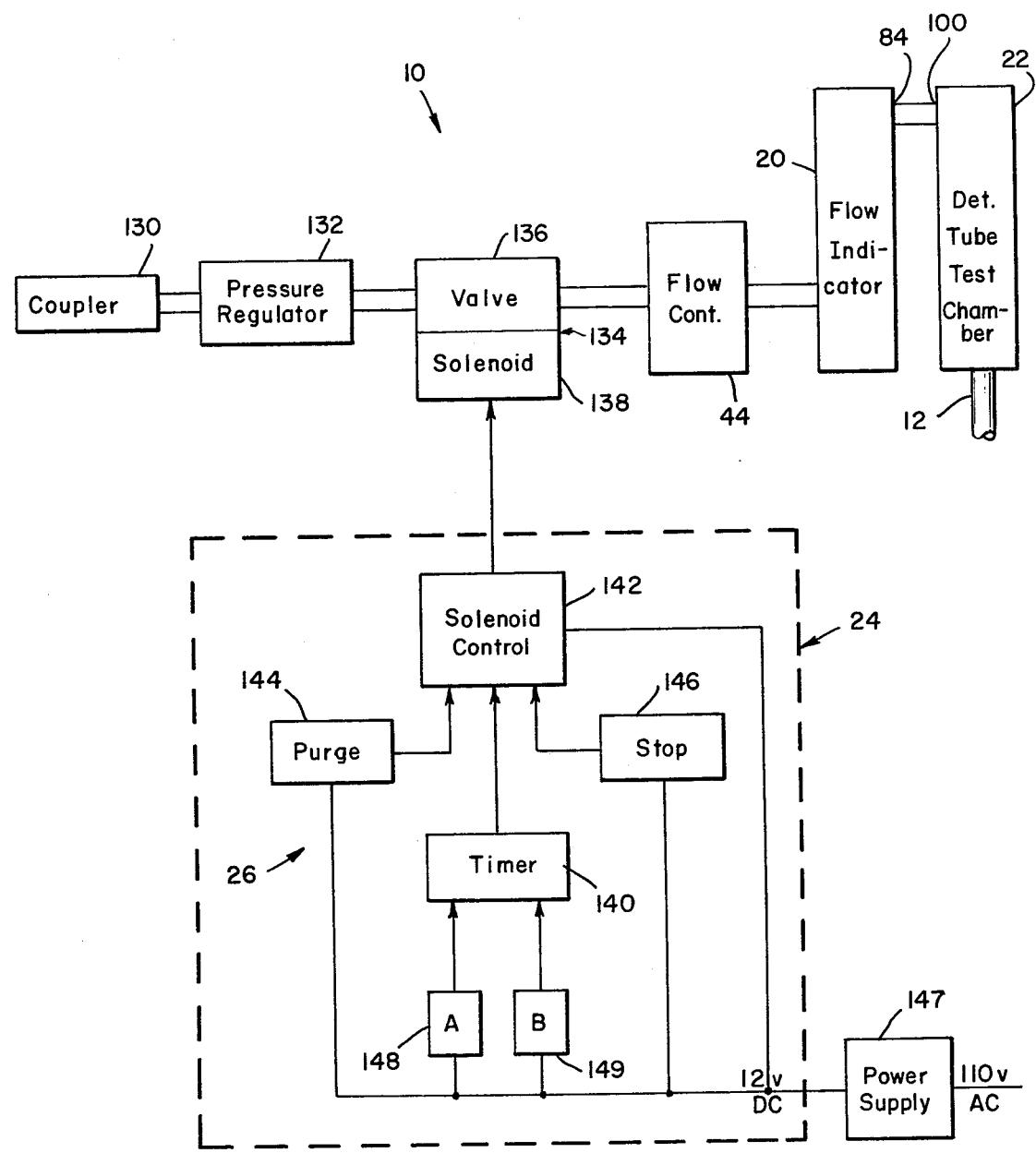
FIG. 4 is a block diagram of the control circuitry and airflow system of the embodiment of FIG. 1.

The block diagram of FIG. 4 shows the operative elements of the monitoring system 10. The air flow passage is shown as comprising a coupling 130 for coupling to a high or low pressure air source and providing the compressed air to a pressure regulator 132 which reduces the pressure to a level suitable for use in the instrument. Usually this pressure will be slightly above atmospheric pressure at sea level. Connected to the output of the pressure regulator 132 is a solenoid-controlled valve 134 comprising an air valve 136 and associated solenoid actuator 138. The solenoid actuator 138 is operable by 12 volts DC. From the valve 136, the air passage extends to the flow control valve 44 of the flow indicator assembly (see FIG. 2) and thence, by interconnected air passages 84, 100, to the detector tube test chamber assembly 22 (see FIG. 3); thereafter to exhaust to atmosphere through port 112.

The control assembly 24 is a replaceable module which can be readily removed from the system 10 and replaced by another one adapted to timing the air flow for different intervals to permit monitoring the presence of a wide variety of contaminants in compressed air. As shown in the block diagram of FIG. 4, the control assembly 24 includes a switch assembly 26, a timer 140 and a solenoid control stage 142. The switch assembly 26 is shown comprising a plurality of individual switches: a purge switch 144, a stop switch 146, and timer select switches 148, 149 (labelled A and B to indicate difference in timing interval for different contaminant tests).

The solenoid control stage 142 is operative, in response to inputs from the timer stage 140 or the purge switch 144 of stop switch 146, to selectively apply 12 volts DC to the solenoid actuator 138, thereby opening and closing the valve 136. 12 volts DC from a power supply 147 is also applied to the switches of the switch assembly 26 and thence to the timer 140 and/or solenoid control stage 142 by the closure of selected switches. Each of the switches 144, 146, 148 and 149 is of the type which contains self-illuminated means which is activated when the switch is pressed. The timer 140 and solenoid control stage 142 are solid state modules, known in the art—"chips" in the current vernacular—which can be readily replaced, particularly with respect to the timer 140 which may be easily changed within a given assembly 24 if it is desired to equip the assembly 24 with different timing ranges for different contaminants. A programable solid state timer can also be used, controllable from the front panel for example, for infinite variability.

It will be understood that the 12 volts DC may be obtained from an external source, if available, or from a self-contained battery pack if desired, rather than by conversion through the power supply 147 from the 110 volt AC input as shown.

Operation of the System

In describing the operation of the system 10 in the testing of compressed air for contaminants, it will be assumed that the function A of switch 148 is for the testing of either carbon monoxide or carbon dioxide and the function B of switch 149 is for the testing of either water or oil vapor. The selection of the test for either carbon monoxide or carbon dioxide is determined by the selection of the appropriate detector tube 23 for insertion in the detector tube test chamber assembly 22; the time duration of air flow is the same for both contaminants. Similarly, the selection for testing for water or oil vapor is determined by the selection of an appropriate detector tube 23, the time interval being the same for both vapors.

Each detector tube of the standard Draeger type is of the same configuration, being of slender hollow glass construction with a calibrated scale and an arrow for indicating flow direction thereon and containing a suitable test material. The hollow glass tube is sealed at both ends by tips which are to be broken off just prior to use by insertion in the recess 115 of the closure knob 95 and tilting until fracture.

The system of the invention is operated in one of two selectable modes, a PURGE mode and a TEST mode. In the PURGE mode, the purge switch 144 is pressed and the air flow rate is adjusted by means of the flow control valve 44 as determined by the flow meter 60. Purging is done without any detector tube 23 within the detector tube test chamber assembly 22 and continues for a time interval timed by the operator. This time interval is not critical and need not be precisely timed. At the end of the PURGE interval, the stop switch 146 is pressed to terminate the air flow.

The closure member 94 of the test chamber 116 is then removed by turning the knob 95 counterclockwise. An appropriate detector tube 23 is selected and both tips are broken off by bending them after insertion in the recess 115 of the closure knob 95. The upper end of the thus-opened detector tube 23 is then inserted within the bore 96, flow arrow pointing down, away from the closure, where it is retained by the O-ring 110 or 111. The numbers of the scale on the tube 23 are aligned with a line (not shown) on the closure knob 95. Thereafter the closure member and detector tube 23 are inserted into the test chamber 116 and the knob is tightened approximately one turn with the line facing outwardly so that the scale on the detector tube 23 is visible through the cover 118 on the front of the assembly, as shown in FIG. 1. The system 10 is now ready for testing the air for the selected contaminant.

In the TEST mode, the appropriate test switch 148 or 149 is pressed. This illuminates its face to indicate the selected test is in process and the timer 140 becomes operative, through the solenoid control stage 142, to maintain the valve 136 open for the precise time interval corresponding to the selected test. The flow rate with the detector tube 23 installed will be slightly less than the rate which was set during the PURGE mode interval. This is normal and should not be readjusted. To obtain a reading on the detector tube 23, it may be necessary to repeat the test by pushing the same test button and interpreting the resulting indication on the detector tube to allow for test repetition.

Example: Carbon Monoxide Test

Assuming the compressed air is to be tested for carbon monoxide, the PURGE switch 144 is pressed and air flow is adjusted until The black ball 74 (FIG. 2) is aligned with the black indicator mark 72. The stop switch 146 is pressed to terminate purging after approximately one minute. The air flow rate will have been adjusted to equal 0.2 liters per minute.

A carbon monoxide detector tube is then selected, prepared as described above and placed within the chamber 116. The switch 148 is then pressed to initiate the TEST mode. The timer 140 will permit precisely one liter to flow through the tube in the preset five-minute interval and will automatically close the valve 136 at the end of the test interval. If carbon monoxide is present, the white indicator chemical in the detector tube 23 will change color to a brownish-green. The total length of the discoloration is a measure of the contamination in PPM (parts per million). The parts per million are read directly on the detector tube and this reading is compared with a reference figure of maximum allowable parts per million of carbon monoxide contamination as established by the appropriate agencies (U.S. Navy, O.S.H.A., California, etc.). If no reading is obtained during the first test, the test can be immediately repeated and the indication from extent of discoloration divided in two. However, one should not save a detector tube for use in a subsequent test, even if the results in the initial test are negative.

Example: Carbon Dioxide Test

In testing for carbon dioxide, exactly the same procedure is followed as for carbon dioxide, except that a different (carbon dioxide) detector tube 23 is used. If carbon dioxide is present, the chemical in the detector tube changes from white to violet.

Example: Water Vapor Test

In testing for water vapor, the system is operated in the PURGE mode for approximately five minutes on any new installation or hookup and for approximately two minutes on any repeat tests on any one hookup. Air flow is adjusted to a rate of 2.0 liters per minute by aligning the silver ball 76 with the silver marker 70 (see FIG. 2). It will be understood, of course, that the balls 74, 76 are forced upwardly in the tube 62 in accordance with the rate of air flow upwardly through the tube.

Following termination of the PURGE mode, a detector tube containing a material specific to testing for water vapor is opened and inserted within the test chamber as previously described. Thereafter, the test switch 149 (function B for water vapor or oil vapor) is pressed. Responsive to switch 149, the timer 140 maintains the valve 136 open for a preset time period of 12.5 minutes, during which 25 liters of air flow through the detector tube. To obtain an indication, it may be necessary to repeat the TEST mode for from two to four test periods. If the air sample contains water vapor, the indicator material within the detector tube 23 will turn from reddish brown to greenish gray. Again, the total length of the discoloration within the tube is a measure of the contamination, and the concentration in milligrams per cubic meter can be read directly from the tube. Other equivalents (PPM, dew point, etc.) may be obtained from a reference chart.

Example: Oil Vapor Test

In testing for the presence of oil vapor, a suitable detector tube is selected and the purging and testing are conducted in the same fashion as in testing for water vapor (the same timer control switch 149 is pressed) with the following exception. After the test period(s) is concluded, the detector tube 23 is removed from the chamber, is bent at a breaking point (marked on the glass with two dots) so that the outer glass tube and inner reagent ampule break. Care should be exercised, since the ampule contains concentrated sulfuric acid. The detector tube 23 is then replaced in the test chamber and air is permitted to flow through the system for about ten seconds (using the PURGE and STOP switches). This forces the acid into the indicator chemical where the acid stains the white indicator chemical yellowish-brown for approximately one-half inch. Air flow is to be stopped at this point. If the monitored air sample contains oil vapor, the yellowish-brown stain will discolor to a blackish tinge in relation to the concentration of oil vapor. This is compared with a color standard which is included in the container of oil vapor detector tubes. The actual concentration of the oil vapor contaminant is then calculated by the following formula:

$$\text{mg oil/cubic meter} = \frac{\text{color standard (micrograms-}\mu g\text{)}}{\text{total liters of air}}$$

The total liters of air equals the number of time periods times the 25 liters in each test sample. The result of the calculation may then be compared with the maximum allowable degree of oil vapor contamination (five micrograms per cubic millimeter as specified by the agencies mentioned above).

The air monitoring system of the present invention thus provides a simple, virtually foolproof, reliable means of testing for those contaminants which are most likely to be encountered in compressed air, as may be used in self-contained respiratory applications of scuba divers and fire fighters, for example. The system uses a specific detector tube for each type of hazardous gas or vapor which is suspected. These are standard, commercially available tubes which provide a direct reading of the specific contaminant as shown by the length or degree of color change. Testing is readily effected by connecting the system to the air source to be tested, adjusting the flow rate while purging to that which is specified for the detector tube selected, and then testing by simply pushing the appropriate time control switch, which will illuminate. When the switch illumination goes out, the test is complete, and the results can be read directly from the tube. The system is accurate, reliable, inexpensive, easy to operate and can be used virtually anywhere under any conditions. Because the testing is automatic, no calibration of an instrument is necessary. The instrument carries its own supply of 40 detector tubes, which is adequate for extended use before restocking. Should a fault develop in the control module or if it is desired to test for other contaminants, it is a simple matter to replace a given control module with another and subsequent tests can be conducted by simply selecting the appropriate detector tubes, of which approximately 100 or more are listed in the above-referenced bulletin of National Draeger, Inc.

Although there has been described one particular arrangement of an air purity monitoring system in accordance with the invention for the purpose of illustrating the manner in which the invention may be used to advantage, it wll be appreciated that the invention is not limited thereto. Accordingly, any and all modifications, variations or equivalent arrangements which may occur to those skilled in the art should be considered to be within the scope of the invention as defined in the annexed claims.

What is claimed is:

1. A portable air purity monitoring system for monitoring compressed air for respiratory use comprising:
   a housing having an exterior face;
   a first, flow meter, chamber and a second, detector tube, test chamber mounted in operative position on said face;
   means defining an air passage through the system including said first and second chambers in series between inlet and exhaust ports, the exhaust port exhausting to atmosphere, said means including a first valve remotely controllable between open and closed positions to control air flow through said passage and means for coupling the inlet portion to a source of high pressure compressed air;
   a pressure regulator connected in series with the air passage adjacent the inlet port for reducing the pressure of compressed air applied at the inlet port to a predetermined level slightly above atmospheric pressure;
   means for operating said system in a PURGE mode to clear the air passage of prior art samples;
   means coupled in series with the air passage for adjusting the rate of flow through said air passage during the PURGE mode, including a manually operable flow control valve mounted adjacent said first chamber; and
   means for operating said system in a TEST mode, including means for retaining a preselected detector tube within the detector tube test chamber coupled in series with the air passage adjacent the exhaust port and further including an automatic timer located within the housing and coupled to remotely control the first valve, the timer being preset to determine different, alternatively selectable, time intervals for the flow of air through said air passage in order to cause a predetermined sample of air corresponding to the test being run to flow through the detector tube during the TEST mode operating interval.

2. The system of claim 1 further including means mounted along said exterior face for separately storing a plurality of different detector tubes integrally in said housing and segregated by type.

3. The system of claim 1 wherein both the PURGE mode operating means and the TEST mode operating means include means for controlling the first valve between open and closed positions.

4. The system of claim 3, wherein the first valve is solenoid actuated, including solenoid control means coupled to control the application of an actuating potential to the valve solenoid.

5. The system of claim 4 wherein the PURGE mode operating means includes switches coupled to the solenoid control means for selectively controlling the opening or closing of the first valve.

6. The system of claim 4 wherein the automatic timer is coupled to the solenoid control means and is operable to maintain the first valve open during the TEST mode interval, said timer having a plurality of preset time intervals selectable by an operator.

7. The system of claim 6 wherein the TEST mode operating means further includes a plurality of switches coupled to activate the timer for different selectable TEST mode time intervals.

8. An air purity monitoring system for monitoring compressed air for respiratory use comprising:
   a housing having an external mounting panel;
   means defining an air passage through the system between an inlet coupling for coupling to a high pressure source of compressed air and an exhaust port which exhausts to atmosphere;

a pressure regulator coupled in the air passage adjacent the inlet coupling for reducing the pressure of compressed air from said source to a predetermined level slightly above atmosphere pressure;

a first valve in series with the air passage, said valve being remotely controllable from the external panel;

a manually controllable second valve in series in the air passage for controlling flow rate therethrough;

a flow meter serially mounted in the air passage and calibrated to indicate rate of air flow through the air passage;

a detector tube test chamber coupled in series in the air passage for mounting a detector tube to receive air flowing through the air passage prior to exhausting through the exhaust port;

a plurality of switches coupled to control the first valve in a PURGE mode and in a TEST mode, respectively, said switches including at least two test switches for selectively actuating the first valve for different preselected time intervals in testing for different contaminants;

wherein the flow meter, the detector tube test chamber, the second valve, and the plurality of switches are mounted on an exterior face of the mounting panel in positions accessible from the exterior of the housing and the second valve is integrally mounted in an assembly containing the flow meter.

9. The system of claim 8 wherein the plurality of switches includes a purge switch for effecting the opening of the first valve in the PURGE mode and a stop switch for selectively closing the first valve after a preselected interval to terminate the PURGE mode.

10. The system of claim 8 wherein the flow meter comprises a vertically oriented transparent tube having a pair of balls therein, said balls being movable differentially against gravity by the force of air flow to provide different indications of air flow rate, and first and second calibration markers positioned along said tube, the first marker being effective with one of said balls to indicate a first selected flow rate and the second marker being effective with the other ball to indicate a second selected flow rate different from the first selected rate.

11. The system of claim 8 wherein the detector tube test chamber includes the exhaust port at one end and further comprises a closure member spaced from the exhaust port end, said closure member being removable from the chamber and having means for sealingly receiving one end of an elongated detector tube.

12. The system of claim 11 wherein the closure member includes an external knob for use in threading the member in and out of an engaged position in the detector tube test chamber, a central bore having an internal O-ring for sealingly engaging a detector tube, and an air passage extending between the central bore and the external circumferential surface of the closure member.

13. The system of claim 12 wherein the detector tube test chamber includes an air passage extending through a side wall thereof to communicate with the air passage of the closure member when the closure member is in position within the detector tube test chamber.

14. The system of claim 13 further including means defining a closed space between the air passages of the closure member and the detector tube test chamber when the closure member is in position therein, said means including a pair of O-rings encircling the closure member for sealing said space.

15. The system of claim 11 wherein the exhaust port end of the detector tube test chamber is shaped to receive one end of a detector tube and retain the tube in position in sealing engagement with the closure member.

16. The system of claim 12 wherein the closure member includes a central bore having portions of different diameter, each portion having a corresponding O-ring seal, for receiving detector tubes of different sizes.

17. The system of claim 12 wherein the closure knob defines a central tapered recess in the upper face thereof to facilitate breaking open the ends of a detector tube in preparation for use.

18. The system of claim 13 further including means connecting the outlet end of the flow meter to the air passage of the detector tube test chamber.

19. The system of claim 8 further including a timer being operable to control the timing of at least two, distinct, alternatively selectable, time intervals.

20. The system of claim 19 wherein one of the test switches is coupled to the timer to select a first one of said time intervals and another of the test switches is coupled to the timer to select another one of said time intervals, and means coupling the timer to the first valve for remotely controlling the position thereof to permit a predetermined volume of air to flow through a detector tube in the detector tube test chamber during a contaminant test.

21. The system of claim 19 wherein the plurality of switches and the timer are mounted in a unit which is readily removable from the front panel for modification and replacement thereof.

* * * * *